US006906077B1

(12) United States Patent
Pang

(10) Patent No.: US 6,906,077 B1
(45) Date of Patent: Jun. 14, 2005

(54) USE OF NEUROTROPHIC FACTOR STIMULATORS FOR THE TREATMENT OF OPHTHALMIC NEURODEGENERATIVE DISEASES

(75) Inventor: Iok-hou Pang, Grand Prairie, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/856,987
(22) PCT Filed: Dec. 1, 1999
(86) PCT No.: PCT/US99/28385

§ 371 (c)(1),
(2), (4) Date: May 25, 2001

(87) PCT Pub. No.: WO00/32197

PCT Pub. Date: Jun. 8, 2000

Related U.S. Application Data

(60) Provisional application No. 60/110,983, filed on Dec. 3, 1998.

(51) Int. Cl.[7] .............................................. A61K 31/52
(52) U.S. Cl. ....................................... 514/261; 514/912
(58) Field of Search ................................. 514/261, 912

(56) References Cited

U.S. PATENT DOCUMENTS

| 4,550,022 A | 10/1985 | Garabedian et al. ......... 424/127 |
| 5,641,749 A | * 6/1997 | Yan et al. ...................... 514/12 |
| 5,641,750 A | 6/1997 | Louis ............................ 514/12 |

FOREIGN PATENT DOCUMENTS

WO    98/10758    10/1998

OTHER PUBLICATIONS

Van Buskirk, et al., "Predicted outcome from hypotensive therapy for glaucomatous optic neuropathy," Am. J. Ophthalmol., vol. 116(5):636–640, (1993).
Schumer, et al., "The nerve of glaucoma!," Arch. Ophthalmol., vol. 112:37–44, (1994).
Raff, et al., "Programmed cell death and the control of cell survival: lessons from the nervous systems," Science, vol. 262:695–700, (1993).
Anderson, et al., "Effect of intraocular pressure on rapid axoplasmic transport in monkey optic nerve," Invest. Ophthalmol., vol. 13(10):771–783, (1974).
Quigley, et al., "The dynamics and location of axonal transport blockade by acute intraocular pressure elevation in primate optic nerve," Invest. Ophthalmol., vol. 15(8):606–616, (1976).
Mansour–Robaey, et al., "Effects of ocular injury and administration of brain–derived neurotrophic factor on survival and regrowth of axotomized retinal ganglion . . . ," Proc. Natl. Acad. Sci. USA, vol. 91:1632–1636, (1994).

Meyer–Franke, et al., "Characterization of the signaling interactions that promote the survival and growth of developing retinal ganglion cells in culture," Neuron, vol. 15:805–819, (1995).
Cui, et al., "NT–4/5 reduces naturally occurring retinal ganglion cell death in neonatal rats," Neuroreport, vol. 5(15):1882–1884, (1994).
Lewin, et al., "Physiology of the neurotrophins," Ann. Rev. Neurosci., vol. 19:289–317, (1996).
Segal, et al., "Intracellular signaling pathways activated by neurotrophic factors," Ann. Rev. Neurosci., vol. 19:463–489, (1996).
Ebadi, et al., "Neurotrophins and their receptors in nerve injury and repair," Neurochem Int., vol. 30(4/5):347–374, (1997).
Kaplan, et al., "Signal transduction by the neurotrophin receptors," Curr. Opin. Cell Biol., vol. 9:213–221, (1997).
Jelsma, et al., "Different forms of the neurotrophin receptor trkB mRNA predominate in rat retina and optic nerve," J. Neurobiol., vol. 24(9):1207–1214, (1993).
Rickman, et al., "Expression of the protooncogene, trk, receptors in the developing rat retina," Vis. Neurosci., vol. 12:215–222, (1995).
Ugolini, et al., "TrkA, TrkB and p75 mRNA expression is developmentally regulated in the rat retina," Brain Res, vol. 704:121–124, (1995).
Cellerino, et al., "Brain–derived neurotrophic factor/neurotrophin–4 receptor TrkB is localized on ganglion cells and Dopaminergics amacrine cells in the vertebrate retina," J. Comp. Neurol., vol. 386:149–160, (1997).
Gao, et al., "Elevated mRNA expression of brain–derived neurotrophic factor in retinal ganglion cell layer after Optic nerve injury," Invest. Ophthalmol. Vis. Sci., vol. 38(9):1840–1847, (1997).
Lindholm, et al., "Brain–derived neurotrophic factor is a survival factor for cultured rat cerebellar granule neurons and protects them against glutamate–induced neurotoxicity," Eur. J. Neurosci., vol. 5:1455–1464, (1993).
Unoki, et al., "Protection of the rat retina from ischemic injury by brain–derived neurotrophic factor, ciliary Neurotrophic factor, and basic fibroblast growth factor," Invest. Ophthalmol. Vis. Sci., vol. 35(3):907–915, (1994).
Beck, et al., "Brain–derived neurotrophic factor protects against ischemic cell damage in the rat hippocampus," J. Cereb. Blood. Flow Metab., vol. 14:689–692, (1994).
Kirsch, et al., "Evidence for multiple, local functions of ciliary neurotrophic factor (CNTF) in retinal development: expression of CNTF and its receptors and in vitro . . . ," J. Neurochem., vol. 68(3):979–990, (1997).

(Continued)

Primary Examiner—Zohreh Fay
(74) Attorney, Agent, or Firm—Teresa J. Schultz

(57) ABSTRACT

Compositions and methods for the treatment of retina and optic nerve head neuropathy are disclosed. The compositions and methods are particularly directed to the use of neurotrophic factor stimulators, such as AIT-082 (neotrofin), in the treatment of glaucomatous neuropathy.

9 Claims, No Drawings

OTHER PUBLICATIONS

Mey, et al., "Intravitreal injections of neurotrophic factors support the survival of axotomized retinal ganglion cells in adult rats in vivo," *Brain Res.*, vol. 602:304–317, (1993).

Weibel, et al., "Brain–derived neurotrophic factor (BDNF) prevents lession–induced axonal die–back in young rat optic nerve," *Brain Res.*, vol. 679:249–254, (1995).

Graul & Castaner, "AIT–082," *Drugs of the Future*, vol. 22(9):945–947, (1997).

Nabeshima, et al., "Oral administration of NGF synthesis stimulators recovers reduced brain NGF content in aged rats and cognitive dysfunction in basal–forebrain–lesioned rats," *Gerontology*, vol. 40(2):46–56, (1994).

Matsui, et al., "Protective effects of ONO–2506 on neurological deficits and brain infarct volume following 1 week of permanent occlusion of middle cerebral . . . ," *Society for Neurosci. Abstracts*, vol. 24:254, (1998).

Gronborg, et al., "Neuroprotection by a novel compound, NS521," *Society for Neurosci. Abstracts*, vol. 24:1551, (1998).

Aimone, et al., "The $1\alpha,25(OH)_2D_3$ analog CB–1093 induces nerve growth factor in non–human primate brain," *Society for Neurosci. Abstracts*, vol. 24:292, (1998).

Culmsee, et al., "NGF antisense oligonucleotide blocks protective effects of clenbuterol against glutamate–Induced excitotoxicity in vitro and focal cerebral . . . ," *Society for Neurosci. Abstracts*, vol. 24:295, (1998).

Takahashi, N. et al., "Rat retinal ganglion cells in culture," *Exp. Eye Res.*, vol. 53:565–572, (1991).

Shinoda, et al., "Stimulation of nerve growth factor synthesis/secretion by propentofylline in cultured mouse astroglial cells," *Biochem. Pharmacol.*, vol. 39(11):1813–1816, (1990).

Nabeshima, et al., "Impairment of learning and memory and the accessory symptom in aged rat as senile dementia model: oral administration of propentofylline..," *Jpn. J. Psychol. Pharmacol.*, vol. 13:89–95, (1993).

*Ophthalmic Surgery*: Principles of Practice, Ed., G.L. Spaeth, W.B. Sanders Co., Philadelphia, PA, U.S.A., p. 85–87, (1990).

Hammes, et al., "Nerve growth factor prevents both neuroretinal programmed cell death and capillary pathology In experimental diabetics," *Molecular Medicine*, vol. 1(5):527–534, Jul. 1995.

Rathbone, et al., "Physiology and pharmacology of natural and synthetic nonadenine–based purines in the nervous system," *Drug Development Research*, vol. 45:356–372, (1998).

Takeda Chem Ind, Ltd., "New drug prevent treat diabetes complicated comprise benzoquinone hydroquinone form treat . . . ," Derwent Publications, Ltd., London XP–002136481 & JP 05 009114A, Jan. 19, 1993 abstract.

Yamamoto, et al., "Neuroprotective effect of $4^1$–(4–methylphenyl)–$2,2^{1''}$:$6^1$,2–terpyridine trihydrochloride, a novel inducer of nerve growth factor," *Life Sciences*, vol. 59(25/26):2139–2146, (1996).

Nitta, et al., "Oral administration of idebenone induces nerve growth factor in the brain and improves learning..," *Archives of Pharmacology*, vol. 349:401–407, (1994).

Culmsee, et al., "Neuroprotection by drug–induced growth factors," *Pharmacology of Cerebral Ischemia*, $7^{th}$, pp. 333–348, (1999).

Semkova, et al., "Clenbuterol protects mouse cerebral cortex and rat hippocampus from ischemic damage and attenuates glutamate neurotoxicity in clutured hippocampal . . . ," *Brain Research*, vol. 717:44–54, (1996).

Riaz, et al., "A vitamin $D_3$ derivative (CB1093) induces nerve growth factor and prevents neurotrophic deficits in streptozotocin–diabetic rats," *Diabetologia*, vol. 42:1308–1313, (1999).

Gronborg, et al., "Neuroprotection by a novel compound, $NS521^1$," *The Journal of Pharmacology and Experimental Therapeutics*, vol. 290(1):348–353, (1999).

Middlemiss, P.J., et al., (Geerts, Hugo), "AIT—082, a unique purine derivative, enhances nerve growth factor mediated neurite outgrowth from PCI cells," *NeuroScience Letters*, (XP–000905256), vol. 199(2):131–4., p. 402, col. 1, paragraph 6—Col. 2, paragraph 3, and p. 403, Col. 1, paragraph 3.

* cited by examiner

USE OF NEUROTROPHIC FACTOR STIMULATORS FOR THE TREATMENT OF OPHTHALMIC NEURODEGENERATIVE DISEASES

This application claims the benefit of Provisional Application No. 60/110,983, filed Dec. 3, 1998.

The present invention relates to the use of neurotrophic factor stimulators to treat ophthalmic neurodegenerative diseases.

BACKGROUND OF THE INVENTION

Primary open-angle glaucoma (POAG) is a progressive disease leading to optic nerve damage and, ultimately, loss of vision. The cause of this disease has been the subject of extensive studies for many years, but is still not fully understood. Glaucoma results in the neuronal degeneration of the retina and optic nerve head. Even with aggressive medical care and surgical treatment, the disease generally persists causing a gradual loss of retinal neurons (retinal ganglion cells ("RGCs")), a decline of visual function, and ultimately blindness (Van Buskirk et al., *Predicted outcome from hypotensive therapy for glaucomatous optic neuropathy, Am. J. Ophthamol.*, volume 25, pages 636–640 (1993); Schumer et al., *The nerve of glaucoma!, Arch. Ophthalmol.*, volume 112, pages 37–44 (1994)).

Several theories have been proposed to elucidate the etiology of glaucoma. One theory suggests that excessive intraocular pressure (in some cases coupled with genetic defects on the optic nerve head, ROC or the optic nerve) disrupts the normal axonal transport along the optic nerve, eventually leading to RGC injury.

Disturbance of axonal transport of the optic nerve hinders traffic of intracellular molecules between the ROC cell soma and its terminal. Among the intracellular molecules of importance are neurotrophic factors. Neurotrophic factors are peptide molecules which stimulate or otherwise maintain growth of neural tissue. The transport of neurotrophic factors from the brain to the cell body of RGCs is essential to the survival of the RGCs. Deprivation of neurotrophic factors can induce apoptosis of neurons (Raff et al., *Programmed cell death and the control of cell survival: lessons from the nervous system, Science*, volume 262, pages 695–700 (1993)).

Deprivation of neurotrophic factors appears to be a cause of glaucoma-induced RGC apoptosis, as such causal link is supported by a great deal of experimental evidence (see, generally, Anderson et al., *Effect of intraocular pressure on rapid axoplasmic transport in monkey optic nerve, Invest. Ophthalmol.*, volume 13, pages 771–783 (1974); Quigley et al., *The dynamics and location of axonal transport blockade by acute intraocular pressure elevation in primate optic nerve, Invest. Ophthalmol.*, volume 15, pages 606–616 (1976); Mansour-Robaey et al., *Effects of ocular injury and administration of brain-derived neurotrophic factor on survival and regrowth of axotomized retinal ganglion cells, Proc. Natl. Acad. Sci. USA*, volume 91, pages 1632–1636 (1994); Meyer-Franke et al., *Characterization of the signaling interactions that promote the survival and growth of developing retinal ganglion cells in culture, Neuron*, volume 15, pages 805–819 (1995); and Cui et al., *NT-4/5 reduces naturally occurring retinal ganglion cell death in neonatal rats, Neuroreport*, volume 5, pages 1882–1884 (1994)). Such trophic factors include neurotrophins and other cytokines.

The neurotrophin ("NT") family of peptides include nerve growth factor (NGF), brain-derived neurotrophic factor (BDNF), NT-3, NT-4/5 and NT-6. They act by binding to neuron surface receptors, such as TrkA, TrkB, TrkC and p75NTR. The Trk receptors are tyrosine kinases. TrkA is selective for NGF, TrkB is selective for both BDNF and NT-4/5, whereas TrkC is selective for NT-3. After binding, the NT-receptor complex is internalized and transported via the axon to the soma. These receptors undergo ligand-induced phosphorylation and dimerization, and activate a cascade of Ras protein-mediated signal transduction events that affect multiple vital functions of the neuron (Lewin et al., *Physiology of the neurotrophins, Ann. Rev. Neurosci.*, volume 19, pages 289–317 (1997); Segal et al., *Intracellular signaling pathways activated by neurotrophic factors, Ann. Rev. Neurosci.*, volume 19, pages 463–489 (1996); Ebadi et al., *Neurotrophins and their receptors in nerve injury and repair, Neurochem Int.*, volume 30, pages 347–374 (1997); Kaplan et al., *Signal transduction by the neurotrophin receptors, Curr. Opin. Cell Biol.*, volume 9, pages 213–221 (1997)). Thus, these receptors play a fundamental role in the regulation of survival and differentiation of developing neurons and contribute to the maintenance of neuronal machinery in adult life.

In the retina, RNA of both TrkA and TrkB has been observed in RGCs, dopaminergic amacrine cells and the optic nerve ("ON"). Their expression was shown to be highly regulated during neuronal development (see, Jelsma et al., *Different forms of the neurotrophin receptor trkB mRNA predominate in rat retina and optic nerve, J. Neurobiol.*, volume 24, pages 1207–1214 (1993); Rickman et al., *Expression of the protooncogene, trk receptors in the developing rat retina, Vis. Neurosci.*, volume 12, pages 215–222 (1995); Ugolini et al., *Trk, TrkB and p75 mRNA expression is developmentally regulated in the rat retina, Brain Res*, volume 704, pages 121–124 (1995); Cellerino et al., *Brain-derived neurotrophic factor/neurotrophin-4 receptor TrkB is localized on ganglion cells and dopaminergics amacrine cells in the vertebrate retina, J. Comp. Neurol.*, volume 386, pages 149–160 (1997)). The TrkB receptor-selective ligands, BDNF and NT-4/5, have been shown to be efficacious for the protection of RGCs. Numerous studies have shown that these NTs not only improve the survival and neurite outgrowth of ROCs in culture, but also significantly reduce axotomy-induced in vivo damage of the ON and RGCs, as well as stimulate the growth of axonal branches from regenerating RGCs (see, generally, the Anderson et al.; Quigley et al.; Mansour-Robaey et al.; Meyer-Franke et al.; and Cui et al. publications cited above). For example, a single intravitreal injection of 5 µg of BDNF prevented the death of the axotomized RGCs when administered during the first five days after injury (Mansour-Robaey et al., above). In contrast with the loss of nearly half of the axotomized RGCs in the untreated retinas, virtually all RGCs were present one week after a single injection of BDNF on Day 0. Messenger RNA expression of BDNF was significantly elevated in the rat RGC layer after ON injury (Gao et al., *Elevated mRNA expression of brain-derived neurotrophic factor in retinal ganglion cell layer after optic nerve injury, Invest. Ophthalmol. Vis. Sci.*, volume 38, pages 1840–1847 (1997)), further suggesting the potential importance of this NT in retinal recovery.

In addition to these protective effects against mechanical damage at the retina and/or ON, neurotrophins may also be protective against other forms of neuronal insult. By a yet unknown mechanism (but possibly a suppression of the apoptosis cascade), BDNF protects CNS neurons from glutamate neurotoxicity (Lindholm et al., *Brain-derived neurotrophic factor is a survival factor for cultured rat* cerebellar granule neurons and protects them against glutamate-induced neurotoxicity, Eur. J. Neurosci., volume 5, pages 1455–1464 (1993)); and it has been effective in vivo in preventing ischemic cell death in the rat retina (Unoki et al., Protection of the rat retina from ischemic injury by brain-derived neurotrophic factor, ciliary neurotrophic factor, and basic fibroblast growth factor, Invest. Ophthalmol. Vis. Sci., volume 35, pages 907–915 (1994)), and hippocampus (Beck et al., Brain-derived neurotrophic factor protects against ischemic cell damage in the rat hippocampus, J. Cereb. Blood Flow Metab., volume 14, pages 689–692 (1994)).

Ciliary neurotrophic factor (CNTF) is another trophic factor that supports survival of neurons. It is part of a cytokine family structurally unrelated to neurotrophins. Both CNTF and its receptor are expressed by the Müller glia during retinal neurogenesis and differentiation (Kirsch et al., Evidence for multiple, local functions of ciliary neurotrophic factor (CNTF) in retinal development: expression of CNTF and its receptors and in vitro effects on target cells, J. Neurochem., volume 68, pages 979–990 (1997). It may also be useful in preventing glaucomatous neuropathy, since it prevents lesion-induced death of RGCs (Mey et al., Intravitreal injections of neurotrophic factors support the survival of axotomized retinal ganglion cells in adult rats in vivo, Brain Res., volume 602, pages 304–317 (1993)) and ON axonal degeneration, albeit less effective than BDNF (Weibel et al., Brain-derived neurotrophic factor (BDNF) prevents lession-induced axonal die-back in young rat optic nerve, Brain Res., volume 679, pages 249–254 (1995)).

Thus, neurotrophic factors play an ameliorative role in glaucomatous retinopathy, and retinal degeneration in general. These trophic factors, however, are peptide molecules, and are therefore difficult to exploit pharmaceutically due to bioavailability problems generally resident in the pharmaceutical administration of peptides. What are needed, therefore, are non-peptide molecules which stimulate neurotrophic activity in compromised retinal tissues, without the bioavailability problems attendant to the natural peptides.

Several neurotrophic factor stimulators have been reported in the scientific literature, for example, AIT-082 (Graul & Castaner, AIT-082, Drugs of the Future, volume 22, pages 945–947 (1997)), idebenone (Nabeshima et al., Oral administration of NGF synthesis stimulators recovers reduced brain NGF content in aged rats and cognitive dysfunction in basal-forebrain-lesioned rats, Gerontology, volume 40, supplement 2, pages 46–56 (1994)), ONO-2506 (Matsui et al., Protective effects of ONO-2506 on neurological deficits and brain infarct volume following 1 week of permanent occlusion of middle cerebral artery in rats, Society for Neurosci. Abstracts, volume 24, page 254 (1998)), NS521 (Gronborg et al., Neuroprotection by a novel compound, NS521, Society for Neurosci. Abstracts, volume 24, page 1551 (1998)), CB-1093 (Aimone et al., The 1α, 25(OH)$_2$D$_3$ analog CB-1093 induces nerve growth factor in non-human primate brain, Society for Neurosci. Abstracts, volume 24, page 292, (1998)) and Clenbuterol (Culmsee et al., NGF antisense oligonucleotide blocks protective effects of clenbuterol against glutamate-induced excitotoxicity in vitro and focal cerebral ischemia in vivo, Society for Neurosci. Abstracts, volume 24, page 295 (1998)). However, nowhere in the art has it been disclosed or suggested to use neurotrophic factor stimulators to treat glaucoma or other ophthalmic neuropathies.

SUMMARY OF THE INVENTION

The present invention is directed to compositions and methods for treating glaucomatous neuropathy and retinal degenerative diseases. The compositions and methods comprise neurotrophic factor stimulators for the treatment of compromised or at risk retinal or optic nerve head tissue.

The neurotrophic factor stimulators are compounds which stimulate the production or activity of retinal neurotrophic factors. The stimulation of neurotrophic factors in the eye ameliorates the conditions of glaucomatous neuropathy and other retinal and optic nerve head degenerative diseases.

Preferred compositions and methods are directed to the neurotrophic factor stimulators, AIT-082 (neotrofin) and idebenone.

DETAILED DESCRIPTION OF THE INVENTION

The present invention is directed to compositions and methods for treating glaucomatous neuropathy and other retinal or optic nerve head degenerative diseases. The compositions comprise one or more neurotrophic stimulator(s) in a pharmaceutically acceptable vehicle.

As used herein, "neurotrophic factor stimulators" refer to those compounds which increase the in situ production or activity of neurotrophic factors in the retina. As used herein, "neurotrophic factor" refers to NGF, BDNF, NT-3, NT-4/5, NT-6, CNTF or other trophic factors which prevent, treat or ameliorate retinal neuropathy. Examples of neurotrophic factor stimulators include: AIT-082 (neotrofin), idebenone, ONO-2506, CB-1093, NS521 ((1-(1-butyl)-4-(2-oxo-1-benzimidazolone)piperidine) SS-701, KT-711 and clenbuterol. The most preferred neurotrophin stimulator of the present invention is AIT-082 (neotrofin). The preceding molecules may be obtained commercially or may be synthesized by methods known to those skilled in the art.

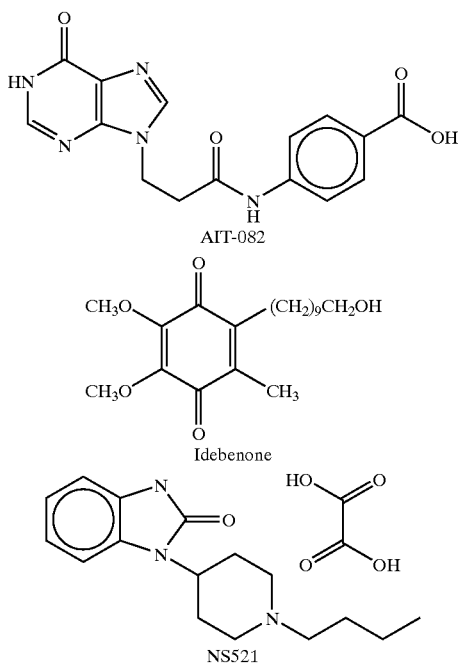

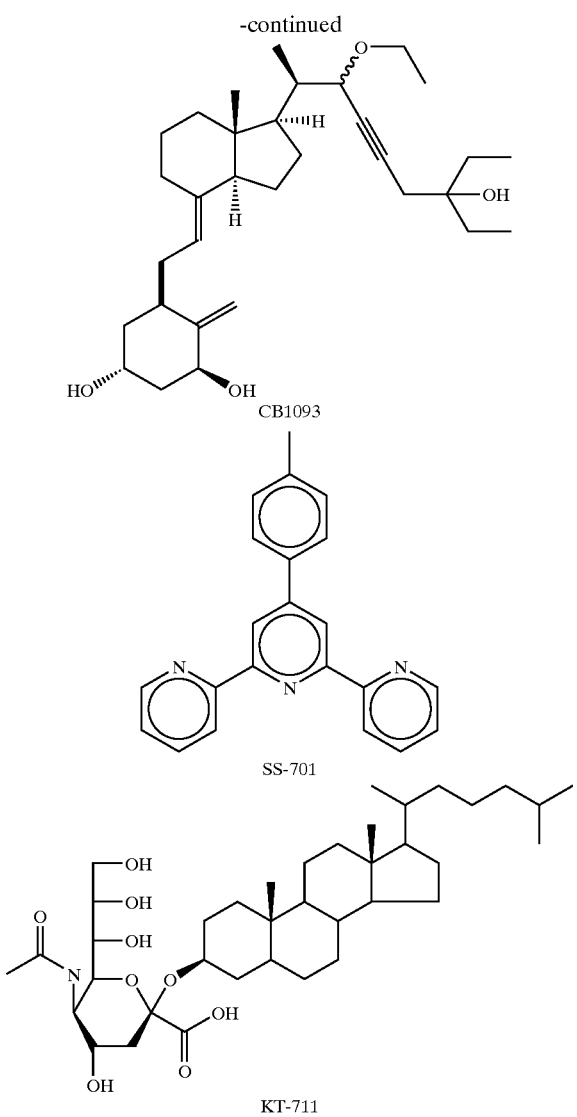

EXAMPLE 1

The following example demonstrates the protective efficacy of a neurotrophic factor stimulator (propentofylline) against retinal cell insult.

Retinal Ganglion Cell Survival Assay:

Techniques for the isolation and culture of RGCs were adapted from those reported by Takahashi N. et al., *Rat retinal ganglion cells in culture. Exp. Eye Res.* volume 53, pages 565–572 (1991). The procedure involved the retrograde labeling of ganglion cells by injecting a fluorescent dye, Di-I, into the superior colliculi. Two to 4 days later, retina cells were dissociated. Cultured RGCs were identified by sufficient Di-I fluorescence to be observed visually using a fluorescent microscope.

Neonatal, Sprague-Dawley rats, 2–5 days old, were anesthetized by hypothermia, after which, a 2 mm midline opening was made in the scalp just caudal to the traverse sinus. The tip of the injection needle (30 gauge) was inserted 6 mm below the top of the skull, and a 5 μl Di-I solution, containing 3 mg/ml Di-I (1,1'-dioctadecyl-3,3,3',3'-tetramethylindo-carbocyanine perchlorate (Molecular Probes, Eugene, Oreg.) in 90% ethanol and 10% dimethylsulfoxide, was injected. The wound was then covered with a drop of Flexible Collodion (Amend Drug & Chemical Co., Irvington, N.J.). Rats were returned to their mother after warming and recovery from anesthesia.

Two to 4 days after Di-I injection, rats were anesthetized by hypothermia and sacrificed by decapitation. Their eyes were enucleated and placed in Dulbecco's modified Eagle's medium: Nutrient mixture F12 (1:1; DMEM/F12, Gibco Co., Grand Island, N.Y.). The retina from each eye was detached and isolated. Retinal cells were dissociated by combining 12 retinae with 5 ml of papain solution, containing 10 mg papain (34 units/ml; Sigma Chemical Co., St. Louis, Mo.), 2 mg DL-cysteine (3.3 mM; Sigma, St. Louis, Mo.) and 2 mg bovine serum albumin (0.4 mg/ml; Sigma) in 5 ml of DMEM/F12, for 25 min at 37° C., then washed 3 times with 5 ml RGC medium (DMEM (Gibco), supplemented with 10% fetal bovine serum (Hyclone, Logan, Utah), 4 mM glutamine (Gibco), 100 units/ml penicillin and 100 μg/ml streptomycin (Sigma). Additional RGC medium was added to the retinal pieces to a final total volume of 40 ml. Retinal pieces were triturated by passing through a disposable pipette several times until cells were dispersed. Cell suspension (1.5 ml; containing approximately $4.5 \times 10^6$ cells) was placed into each of the poly-D-lysine coated glass bottom culture dishes. The cells were cultured for 3 days in 95% air/5% $CO_2$ at 37° C.

Fetal calf serum was removed from the culture medium 3 days after the cells were isolated with or without various therapeutic agents. Three days later, the cells were observed with a fluorescent microscope at 200× magnification, and Di-I-labeled fluorescent cells in 20 microscopic fields were counted and averaged. The results are illustrated in Table 1, below:

TABLE 1

Effects of a neurotrophic factor stimulator on RGC survival

| Cultured with Serum | Agent | RGC Survival (%) |
|---|---|---|
| Yes | None | 100.0 ± 4.9* |
| No | None | 46.4 ± 5.6 |
| No | BDNF (5 μM) + Forskolin (10 ng/ml) | 79.9 ± 5.4* |
| No | Propentofylline (100 μM) | 96.9 ± 4.8* |

Note:
RGC survival in the presence of serum defines 100%. All values are expressed as mean and SEM (n = 6).
*represented p < 0.05 versus the no-serum, no-drug group by one-way ANOVA then Dunnett's test.

Table 1 illustrates that the survival of RGCs was greater in the presence of fetal calf serum (and the endogenous neurotrophic factors contained in the serum). The neurotrophic factor, BDNF, in the presence of forskolin, appeared to protect against such insult (i.e., removal of the fetal calf serum). Similarly, propentofylline, which is known to stimulate the production of nerve growth factor in cultured astrocytes (Shinoda et al., *Stimulation of nerve growth factor synthesis/secretion by propentofylline in cultured mouse astroglial cells, Biochem. Pharmacol.*, volume 39, pages 1813–1816 (1990)) and in aged rat brain in vivo (Nabeshima et al., *Impairment of learning and memory and the accessory symptom in aged rat as senile dementia model: oral administration of propentofylline produces recovery of reduced NGF content in the brain of aged rats, Jpn. J. Psychol. Pharmacol.*, volume 13, pages 89–95 (1993)), also protected the cells against the serum deprivation-induced cell death. These data indicate that compounds that stimulate neurotrophic factor production or increase their activity may protect retinal cells, especially RGCs, against injury induced by deprivation of neurotrophic factors.

The methods of the present invention comprise administering to a human patient one or more neurotrophic factor stimulators for the treatment of retinal or optic nerve head neuropathy.

The methods of the present invention are particularly directed to the use of neurotrophin factor stimulators for the treatment of glaucoma, and other diseases and disorders of the outer retina, particularly age related macular degeneration, retinal ischemia, acute retinopathies associated with trauma, post-surgical complications, the damage associated with laser therapy including photodynamic therapy (PDT), and surgical light induced iatrogenic retinopathy. As used herein, "retina or optic nerve head neuropathy" refers to any of the foregoing diseases or other retinal or optic nerve head neurodegenerative diseases.

The neurotrophic factor stimulators of the present invention may be contained in various types of pharmaceutical compositions, in accordance with formulation techniques known to those skilled in the art. In general, the neurotrophic factor stimulators will be formulated in solutions or suspensions for topical ophthalmic or intraocular administration, or as tablets, capsules or solutions for systemic administration (e.g., oral or intravenous).

Oral formulations of the neurotrophin stimulators are preferred due to ease of administration. Oral formulations may be in liquid or solid form. In general, oral formulations will contain the active neurotrophin factor stimulator and inert excipients. In general, solid tablet or capsule dosages will contain various excipients such as bulking agents, binding agents, time release coatings, or other agents known to those skilled in the art. Liquid dosages will contain carriers, buffers, tonicity agents, solubilizing agents, or other agents known to those skilled in the art.

The compositions of the present invention may be administered intraocularly following traumatic and/or other acute ischemic events involving the retina and optic nerve head tissues or prior to or during surgery to prevent ischemic damage or injury. Compositions useful for intraocular administration will generally be intraocular injection compositions or surgical irrigating solutions. Intraocular injection compositions will generally be comprised of an aqueous solution, e.g., balanced salt irrigating solutions, discussed below.

When the neurotrophin factor stimulators are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian et al.), the entire contents of which are incorporated herein by reference. Retrobulbar and periocular injections are known to those skilled in the art and are described in numerous publications including, for example, *Ophthalmic Surgery: Principles of Practice*, Ed., G. L. Spaeth, W.B. Sanders Co., Philadelphia, Pa., U.S.A., pages 85–87 (1990).

In general, the doses utilized for the above described purposes will vary, but will be in an effective amount to prevent, reduce or ameliorate retina or optic nerve head neuropathy. As used herein, "pharmaceutically effective amount" refers to that amount of a neurotrophin factor stimulator which prevents, reduces or ameliorates retina or optic nerve head neuropathy. The neurotrophic factor stimulators will generally be contained in the topical or intraocular formulations contemplated herein in an amount of from about 0.001 to about 10.0% weight/volume ("% w/v").

Preferred concentrations will range from about 0.1 to about 5.0% w/v. Topical formulations will generally be delivered to the eye one to six times a day, at the discretion of a skilled clinician. Systemic administration compositions will generally contain about 10–1000 mg of a neurotrophic factor stimulator, and can be taken 1–4 times per day, at the discretion of a skilled clinician.

As used herein, the term "pharmaceutically acceptable carrier" refers to any formulation which is safe, and provides the appropriate delivery of an effective amount of at least one neurotrophic factor stimulator for the desired route of administration.

The compositions of the present invention may contain additional pharmaceutically active agents or may be dosed concurrently with other pharmaceutical compositions. In particular, when treating a mammal for the prevention, treatment or amelioration of glaucomatous retinopathy, the compositions of the present invention may contain additional "anti-glaucoma" agents or may be dosed concurrently or sequentially with anti-glaucoma agent compositions. Examples of anti-glaucoma agents include: prostaglandins or prostanoids, carbonic anhydrase inhibitors, beta-adrenergic agonists and antagonists, alpha-adrenergic agonists or other anti-glaucoma agents known to those skilled in the art.

EXAMPLE 2

Topical Compositions useful for Treating Glaucomatous Neuropathy:

| Component | % (w/v) |
| --- | --- |
| AIT-082 (Neotrofin) | 0.1–2.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. |

EXAMPLE 3

A Preferred Topical Composition useful for Treating Glaucomatous Neuropathy:

| Component | % (w/v) |
| --- | --- |
| AIT-082 (Neotrofin) | 0.5–1.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

AIT-082 is sterilized by either dry heat or ethylene oxide. If ethylene oxide sterilization is selected, aeration for at least 72 hours at 50° C. is necessary. The sterilized compound is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the BPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 4

Formulation for Oral Administration:

Tablet:

1–1000 mg of a neurotrophic factor stimulator with inactive ingredients such as starch, lactose and magnesium stearate can be formulated according to procedures known to those skilled in the art of tablet formulation.

EXAMPLE 5

Preferred Formulation for a Topical Ocular Solution:

| Component | % (w/v) |
| --- | --- |
| AIT-082 (Neotrofin) | 0.5–1.0 |
| Benzalkonium chloride | 0.01 |
| HPMC | 0.5 |
| Sodium chloride | 0.8 |
| Sodium phosphate | 0.28 |
| Edetate disodium | 0.01 |
| NaOH/HCl | q.s. pH 7.2 |
| Purified Water | q.s. |

EXAMPLE 6

A Preferred Formulation for Oral Administration:

Tablet:

50–500 mg of AIT-082 (Neotrofin) with inactive ingredients such as starch, lactose and magnesium stearate can be formulated according to procedures known to those skilled in the art of tablet formulation.

The invention in its broader aspects is not limited to the specific details shown and described above. Departures may be made from such details within the scope of the accompanying claims without departing from the principles of the invention and without sacrificing its advantages.

I claim:

1. A method for the treatment of retina or optic nerve head neuropathy associated with glaucoma which comprises administering to a mammal a composition comprising an effective amount of one or more non-peptide neurotrophic factor stimulator(s) and a pharmaceutically acceptable vehicle, wherein the non-peptide neurotrophic factor stimulator is selected from the group consisting of: AIT-082 (neotrofin), ONO-2506, CB-1093, NS521 ((1-(1-butyl)-4-(2-oxo-1-benzimidazolone) piperidine, SS-701, KT-711 and clenbuterol, and wherein said composition is administered topically or intraocularly.

2. A method according to claim 1, wherein the neurotrophic factor stimulator is AIT-082 (neotrofin).

3. The method of claim 1, wherein the composition is administered by intraocular injection prior to ocular surgery.

4. The method of claim 1, wherein the composition is administered by intraocular injection during ocular surgery.

5. The method of claim 1, wherein the composition is administered by intraocular injection prior to and during ocular surgery.

6. The method of claim 3, wherein the composition is a balanced salt irrigating solution.

7. The method of claim 4, wherein the composition is a balanced salt irrigating solution.

8. The method of claim 5, wherein the composition is a balanced salt irrigating solution.

9. The method of claim 3, wherein the composition is administered through retrobulbar or periocular injection.

* * * * *